(12) United States Patent
Chaykovskyy (10) Patent No.: US 9,451,901 B2
(45) Date of Patent: Sep. 27, 2016

(54) METHOD AND DEVICE FOR EVALUATION OF MYOCARDIAL DAMAGES BASED ON THE CURRENT DENSITY VARIATIONS (76) Inventor: Illya Anatoliiovych Chaykovskyy, Kiev (UA)

( * ) Notice: Subject to any disclaimer, the term of this patent is extended or adjusted under 35 U.S.C. 154(b) by 76 days.

(21) Appl. No.: 14/376,928

(22) PCT Filed: Sep. 7, 2012

(86) PCT No.: PCT/UA2012/000083
§ 371 (c)(1),
(2), (4) Date: Aug. 6, 2014

(87) PCT Pub. No.: WO2014/011135
PCT Pub. Date: Jan. 16, 2014

(65) Prior Publication Data
US 2015/0011862 A1  Jan. 8, 2015

(30) Foreign Application Priority Data
Jul. 13, 2012  (UA) .............................. A 2012 08663

(51) Int. Cl.
*A61B 5/05* (2006.01)
*A61B 5/04* (2006.01)
*A61B 5/00* (2006.01)

(52) U.S. Cl.
CPC ............. *A61B 5/05* (2013.01); *A61B 5/04007* (2013.01); *A61B 5/7275* (2013.01)

(58) Field of Classification Search
CPC ............ A61B 5/00; A61B 5/04; A61B 5/05; A61B 5/04005; A61B 5/04007
See application file for complete search history.

(56) References Cited

U.S. PATENT DOCUMENTS 3,824,990 A  7/1974  Baule
2004/0034299 A1  2/2004  Kandori et al.

FOREIGN PATENT DOCUMENTS

CN  1221325 A  6/1999
CN  1552285 A  12/2004
(Continued)

OTHER PUBLICATIONS

"Magnetocardiography in Early Detection of Electromagnetic Abnormality in Ischemic Heart Disease" by S. Watanabe et al. J Arrhythmia. vol. 24, No. 1, pp. 4-17, 2008.*
(Continued)

*Primary Examiner* — Tse Chen
*Assistant Examiner* — Jason Ip
(74) *Attorney, Agent, or Firm* — Cozen O'Connor (57) ABSTRACT

Invention is related to cardiology and intended for diagnosis of ischemic myocardial injuries. Magnetocardiographic examination is executed, current density vectors maps are reconstructed during ST-T interval and 4 sub-intervals of QRS complex, quantitative diagnostic indicators are calculated. Characterized in that, for said time intervals total length of all vectors (total current), autocorrelation coefficient of the instant map and its correlation with map onto the T wave peak are derived, several quantitative indicators for these curves are calculated (area under the curve, time intervals, their ratio, etc.) and ranges of their values are divided onto 3 intervals. As a result, absence/presence of ventricles injuries is diagnosed according to the rule—injury is absent (presence minor, significant), if certain quantitative indicator is ranged in one of 3 said intervals or if score of points for separate quantitative indicators is less than or equal to 7 (8-16, 17 and more).

3 Claims, 2 Drawing Sheets

(56) References Cited

FOREIGN PATENT DOCUMENTS

| CN | 1926553 A | 3/2007 |
|---|---|---|
| EP | 1769741 A1 | 4/2007 |
| KR | 1020060117545 | 11/2006 |
| UA | 77722 C2 | 1/2006 |
| UA | 77723 C2 | 1/2006 |
| UA | 74466 C2 | 12/2006 |
| UA | 20101 U | 1/2007 |
| UA | 21299 U | 3/2007 |
| UA | 83050 C2 | 6/2008 |
| UA | 83061 C2 | 6/2008 |
| UA | 90701 C2 | 5/2010 |
| UA | 100929 C2 | 12/2012 |
| WO | 0120477 A2 | 3/2001 |
| WO | 0217769 A2 | 3/2002 |
| WO | 2005002313 A2 | 1/2005 |
| WO | 2012173583 A1 | 12/2012 |

OTHER PUBLICATIONS

Chaikovsky, I., "Magnetocardiography in unshielded location in coronary artery disease detection using computerized classification of current density vectors maps", Dr. Med. Dissertation, University Duisburg-Essen, Germany, 2006.

International Search Report of PCT/UA2012/000083 dated as mailed Apr. 18, 2013.

Schupback, W., et al., "Non-invasive diagnosis of coronary artery diease using cardiogoniometry performed at rest", Swiss Medical Weekly, 2008, vol. 138, Nos. 15-16, pp. 230-238, www.smw.ch.

* cited by examiner

METHOD AND DEVICE FOR EVALUATION OF MYOCARDIAL DAMAGES BASED ON THE CURRENT DENSITY VARIATIONS

FIELD OF INVENTION

Present invention is related to the field of medicine, namely—to cardiology, and could be used for diagnosis of electrophysiology damages and other myocardial injuries. Currently, reliable diagnosis for most of the heart diseases remains the clinical issue of today.

PRIOR STATE-OF-ART

For example, for diagnosis of the myocardial ischemia by means of the most widely used method of the heart electrical activity analysis ECG, there are several diagnostic criteria known to be used, characterizing heart EMF vector magnitude and direction in different moments of the cardio-cycle. For example, in the vector-ECG method [Non-invasive diagnosis of coronary artery disease using cardiogoniometry performed at rest, W. Schüpbach, B. Emese, P. Loretan et al, Swiss Medical Weekly, 2008; 138(15-16):230-238, www.smw.ch] there are 13 magnitude and angle indexes are used for diagnosis of the ischemic heart disease (IHD), which characterize re- and depolarization processes.

But this method possesses several significant limitations:

1) There is only sum vector analyzed, which reflects only integral condition of myocardium; as a result, many of the regional electric processes damages remain undetected.

2) Information is used only concerning the potential difference between the body surface points, but not the current density distribution (CDD) inside the myocardium, hence this information could be distorted by non-uniformity of electric properties and anisotropy of body tissues around the heart.

Hereby, diagnostic accuracy of the ECG method is not enough for the clinical diagnosis of IHD. Therefore, further development is reasonable of non-invasive, completely safe methods, non-interfering onto patients, free of contraindications, and hence—which could be repeated may times in different clinical situations. Namely, magnetocardiography (MCG) is completely non-invasive and safe method, providing additional information.

Application perceptiveness of MCG method for the heart pathology diagnosis is grounded on the fact that any other method doesn't allow to determine direction and magnitude of the local currents in myocardium. Only MCG, which detects magnetic field produced by the heart currents, allows direct reconstruction of the cardiac currents density distribution in the heart.

But for CDD reconstruction it's necessary to solve so called inversed magnetostatic problem (IMP), which consists in calculation of the magnetic field sources (currents) by measured magnetic field distribution.

Ability of MCG to provide new useful information that can serve as a marker of abnormal electrophysiological processes in the heart is covered particularly in the documents:

1. WO 0217769, Ischemia identification, quantification and partial localization in MCG, A. Bakharev, Cardiomag Imaging Inc, USA, 2002.

2. WO 002313, Machine learning for classification of magnetocardiograms, Sternickel K. B, Cardiomag Imaging Inc, USA, 2005.

3. Chaikovsky I. Magnetocardiography in unshielded location in coronary artery disease detection using computerized classification of current density vectors maps, Dr. Med. dissertation, University Duisburg-Essen, Germany, 2006.

4. UA 90701. Method for estimation of the abnormality rate of electrical processes in heart's ventricles, IC NASU, MSEC ITiC, Chaikovsky I., Budnyk M., Bull. No. 10, 2010.

5. UA a 2011 07571, Method and device for estimation of the myocardial ischemia degree on the base of the current density distribution maps analysis, I. Chaikovsky, M. Budnyk, 16.06.2011.

6. PCT/UA2011/000121, Method and device for evaluation of myocardial ischemia based on current density maps, I. Chaykovskyy, M. Budnyk, 02.12.2011.

Patent WO 002313 considers diagnostic method, based on the one of automatic image recognition techniques with neural networks (Direct Kernel based Self-Organizing Maps). In terms of this recognition magnetic maps are qualified as normal or pathological.

Limitation of this method is the fact, that it doesn't use solution of the inverse problem of magnetostatics (IPM), and also it allows to qualify maps just by 2 classes (normal and pathological) without further detalization.

In the Ph.D. thesis by I. Chaikovsky "Magnetocardiography in unshielded location in coronary artery disease detection using computerized classification of current density vectors maps" there is diagnostic method analyzed, with reconstruction of the CDD maps set from the J-point (the end of QRS complex) to the end of the T wave, classification of the CDD maps onto 5 grades—from normal to highest pathological grade on the base of directions estimation of the largest current density vectors. Limitations of this method are in that it analyzes only ventricular repolarization and that maps classification is performed only by small amount of classes.

In prototype method UA 90701 technique is considered for estimation of the abnormality rate of electrical processes in heart's ventricles by means of MCG-mapping, analysis of CDD maps from the beginning of QRS complex to the end of T wave, determination of the high current density areas and current vortexes on the maps of topologic parameters, calculation of their difference grades compared to the normal quasi-dipole map and its mean value for the set.

Method is distinctive in that it takes into account areas with low current density and on this base determines the regional non-homogeneity degree (RNH) by the ternary scale—low, medium, high. Then there is magnitude ratio calculated R/T of the largest current density vectors on the peaks of R and T waves, and on this base degree of global non-homogeneity (GNH) is determined by the ternary scale: low—with $4<R/T<6$, medium—with $6<R/T<8$, high—with $R/T>8$.

As a result, conclusion is made concerning abnormality degree by five-level scale—"normal" for low RNH degree and GNH, "low abnormality level"—for low RNH degree and medium GNH degree and vise versa, "medium abnormality level"—for low RNH degree and high GNH degree and vise versa, or for medium degree of RNH and GNH, "high abnormality level"—for medium RNH degree or high GNH degree and vise versa, "very high abnormality level"—for high degree of RNH and GNH.

So, prototype makes it possible to identify abnormality degree of myocardium CDD deviation vs. normal conditions in consequence of the damage of electrical processes in the heart's ventricles. However, it also has disadvantages, because index is calculated on the basis of current vectors at certain moments of time—on the peaks of waves R and T, rather than averaged over the cardio-cycle period. Averaged index is less sensitive to short-period interferences and to the interpersonal dispersion of physiological parameters.

Patent WO 0217769 considers corresponding method for the IHD diagnosis, where IHD is classified onto 4 severity degrees with presence of changes in vertical coordinate (depth) of the effective dipole during ST-segment. Herewith 1-st (2-nd, 3-rd or 4-th) degree of IHD occurs if dipole depth changes only during the 1-st quarter (2, 3 first quarters or during the whole ST-segment). In health people without IHD, dipole depth has practically constant value.

Prototype advantage lies in the fact that:

1) There are quantitative parameters analyzed on the base of inverse problem solution, but not magnetic field maps (MFM);

2) Variations of these parameters are taken into account during the certain cardiocycle interval.

Limitation of this analog method is that described inverse problem (IP) is solved in dipole approximation, and also in approximation of the magnetic, but not of the current dipole, which doesn't correspond to the real electrophysiological processes in heart. Analysis on the base of dipole model is simplified, that is why more sophisticated representations should be used in the form of CDD maps in the frontal plane. CDD map—is a vector field, where each vector represents current density in given point, and areas of the map with local maximums surrounded by the lower magnitude vectors, represent separate electrical activity zones of myocardium. Also depolarization process is not analyzed.

Prototype method PCT/UA2011/000121 (UA a 2011 07571) covers method for evaluation of myocardial ischemia degree based on the current density CDD maps, intended for diagnosis of electrophysiology disorders and other myocardial injuries. According to this method, MCG examination is carried out; CDD maps are reconstructed in the frontal plane, current density vectors lengths are calculated for each map during ST-T interval and QRS complex. Method is characterized in that for the ST-T and 4 subintervals of QRS there are 3 angular vectors direction sectors allocated—normal normal, intermediate and abnormal, which represent depolarization of the interventricular septum 1, anterior wall and apex of the left ventricle 2, left ventricle side wall 3, basal myocardial regions 4. Then total length is calculated for each map of the vectors directed in normal (LNORM), abnormal (LPATH) and intermediate (LI) sector, instantaneous abnormality indexes AI=100× LNORM/(LNORM+LPATH+½×LI) and their average value for each Alave interval. As a result, for the regions 1-4 ischemia absence or presence is diagnosed (non-significant, significant), if Alave falls into the interval 70≤Alave≤100 or 40≤Alave≤70 (0≤Alave≤40). Device contains at least one electronic module, performs at leas one calculation stage and can include embedded microcontroller, or at least one stage is performed using computer software.

Advantage of the prototype method is using CDD maps instead of MFM, using the average relative abnormality index Alave instead if instantaneous indexes and partitioning of QRS complex, which characterizes the process of depolarization, onto 4 sub-intervals. All this makes it possible to analyze individual phase of ventricles excitation and as a result—to identify ischemization degree for the one of four myocardium regions.

Drawback of the prototype method is consideration only of amplitudes and directions of the current density vectors, while other quantitative parameters of maps are not taken into account. Another disadvantage—is application of averaged index, which doesn't allow considering it's time variations.

Thus, advantages of proposed method for diagnosis of ischemic myocardial injuries compared to the prototype are:

1) Instead of amplitude-angular parameters of the current density vectors, using another integral quantitative indicators of the CDD maps (total current, correlation, autocorrelation), which in summary accounts variations of CDD maps in general.

2) Additional application of generalized scoring index, which is the sum of points corresponding to the absence or presence of different grades of ventricle injuries (minor, significant);

3) Accounting of time variations of the quantitative indexes, calculated on the base of CDD maps.

SUMMARY OF THE INVENTION

The basis of the present invention tasked with improving the method of diagnosis, by introduction of the new additional indicators, application of empirically defined limits of these parameters, introduction of additional actions to calculate numerical values of these parameters and diagnostic rules determining the absence or presence of myocardial damages, and if any—degree of their severity (minor or significant).

To solve the task using proposed method, magnetic field maps are recorded, CDD maps reconstructed, total current maps are calculated as lengths sum of the current vectors, correlation coefficient between the current map and the map on top of the T wave and autocorrelation coefficient are determined, variation curves of these parameters are built for each phase of ventricular depolarization and repolarization, values, that describe the shape and duration of certain intervals these curves are calculated separately for each of these phases, conclusions are made based on these values, device is implemented with electronic modules, including using the microprocessors or computer programs.

Assigned task in the method for evaluation of myocardial damages based on the current density variations of indexes of the current density distribution (CDD) maps is solved by:

1) Execution of magnetocardiographic examination;

2) CDD maps reconstruction in the frontal plane and calculation of the current density vector magnitudes in each map during the overall cardio-cycle;

3) Calculation of the total current for each map during the overall cardio-cycle;

4) Plotting the total current time variation curve during the ST-T interval;

5) On the base of total current variation curve, according to item 4, calculation of the ST segment duration (point J-T wave beginning);

6) Calculation of the ratio of ST segment duration, according to item 5, to the overall ST-T interval duration;

7) Diagnosis of the ventricles injuries absence/presence according to the rule—injury is absent (minor, significant), if intervals ratio, according to item 6, is less than 25% (25-35%, more than 35%);

8) Calculation of the total current curve during QRS complex (Q point-J point), which represents total ventricles depolarization;

9) Diagnosis of the ventricles injuries absence/presence according to the rule—injury is absent (minor, significant), if QRS complex duration, according to item 8, is less than 0.11 s (0.11-0.14 s, more than 0.14 s);

10) Total current curves calculation for 4 time subintervals of the QRS complex, which represent depolarization of the interventricular septum (1), anterior wall and apex of the left ventricle LV (2), left ventricle side wall (3), basal myocardial regions (4);

11) Ratio calculation of 4 sub-intervals, according to item 10, to "appropriate" duration values, known from electrophysiology;

12) Diagnosis of absence/presence of (minor, significant) injury of myocardial regions (1)-(4) noted in item 10, if one of 4 sub-intervals ratio ranges from 0.8 to 1.2 (0.7-0.8 and 1.2-1.5, lower than 0.7 and higher than 1.5);

13) Arithmetic mean value calculation of 4 sub-intervals ratios, calculated in item 11;

14) Diagnosis of the ventricles injuries absence/presence according to the rule—injury is absent (minor, significant), if arithmetic mean value, according to item 13, is ranged from 0.8 to 1.2 (0.7-0.8 and 1.2-1.5, lower than 0.7 and higher than 1.5);

15) In the case if during QRS complex there are negative waves occur, their quantity is counted;

16) Diagnosis of the ventricles injuries absence/presence according to the rule—injury is absent (minor, significant), if number of negative waves in QRS complex is less than 1 (is 2-3, more than 3);

17) Dependence calculation of the correlation coefficient for the instant map with map taken on the T wave peak during ST-T interval;

18) On the base of correlation curve, according to item 17, calculation of the ST segment duration (point J-T wave beginning);

19) Calculation of the ratio of ST segment duration, according to item 18, to the overall ST-T interval duration;

20) Diagnosis of the ventricles injuries absence/presence according to the rule—injury is absent (minor, significant), if intervals ratio, according to item 19, is less, than 25% (25-35%, more than 35%);

21) Difference calculation between the maximum correlation coefficient on the T wave peak (which is equal to 1 by definition) and its value in the 4-th point of ST-T interval (40 ms after J point);

22) Diagnosis of the ventricles injuries absence/presence according to the rule—injury is absent (minor, significant), if said difference according to item 21, is less than 30% (30-50%, more than 50%);

23) Average correlation coefficient is calculated on the ST-T interval;

24) Diagnosis of the ventricles injuries absence/presence according to the rule—injury is absent (minor, significant), if average coefficient according to item 23, is more than 75% (60-75%, less than 60%);

25) Time dependence calculation of the correlation coefficient for the instant map with map on the R wave peak during QRS complex;

26) Diagnosis of the ventricles injuries absence/presence according to the rule—injury is absent (minor, significant), if correlation curve according to item 25 contains two (one, none) characteristic inflection points in the moments of rapid curve increase or decrease;

27) Time dependence calculation of the autocorrelation coefficient for the instant map during QRS complex;

28) Diagnosis of the ventricles injuries absence/presence according to the rule—injury is absent (minor, significant), if autocorrelation curve according to p. 27 contains two (one, none) expressed local minimums;

29) Assigning diagnosis "absence of injuries" 0 points, "presence of minor (significant) injury" 1(2) points;

30) Diagnosis of the ventricles injuries absence/presence according to the rule—injury is absent (minor, significant), if the sum of points according to p. 29 for individual quantitative indicators according to items 7, 9, 12, 14, 16, 18, 20, 22, 24, 26, 28 is less than or equal to 7 (8-16, 17 and more);

31) Performing of calculations for at least one of items 3-30 using device, including at least one electronic unit, controlled by embedded microprocessor;

32) Implementation of the device according to item 31 in such a way that it's controlled by external computer.

The novelty of proposed solution compared to the current state of art:

1) Using new quantitative CDD indicators (total current, correlation, autocorrelation) on the base of IPM in order to obtain more reliable estimation of the presence and severity grade of the myocardial injuries;

2) Using of the different types of quantitative indicators, e.g. time, current, correlation;

3) Combining different kinds of indicators for formulation of the diagnostic decision on the base of generalized score criterion;

4) Accounting of time variations of the quantitative indexes, calculated on the base of CDD maps.

Technical result consists in:

1) Improvement of injuries detection reliability;

2) Possibility to provide more accurate estimation of existence and severity grade of myocardial injuries;

3) Possibility to determine injury localization.

BRIEF DESCRIPTION OF THE DRAWINGS

Brief Description of Figures

FIG. 2. Total current curve during ST segment (J point—beginning of the T wave). Vertical marker allocates the beginning point of T wave rise: A) absence of injury; B) significant injury.

FIG. 3. Total current curve during QRS complex (Q point—J point), which represents total ventricles depolarization. Vertical marker allocates point corresponding to the T wave peak: A) absence of injury; B) significant injury.

FIG. 4. Time dependence curve of the correlation coefficient during ST-T interval for the instant map with map on the T wave peak: A) absence of injury; B) significant injury.

FIG. 5. Time dependence curve during QRS complex of the coefficients of correlation for the instant map with map on the R: A) absence of injury; B) significant injury.

FIG. 6. Time dependence curve during QRS complex of the coefficients of autocorrelation for the instant map: A) absence of injury; B) significant injury.

DESCRIPTION OF THE PREFERRED EMBODIMENTS

In its main implementation method contains action sequence, executing individual steps of the algorithm, which in consumption implement proposed method. Schematic diagram of the method is represented on FIG. 1, where dashed steps don't describe proposed method, but represented just to illustrate its background.

Figure 1:
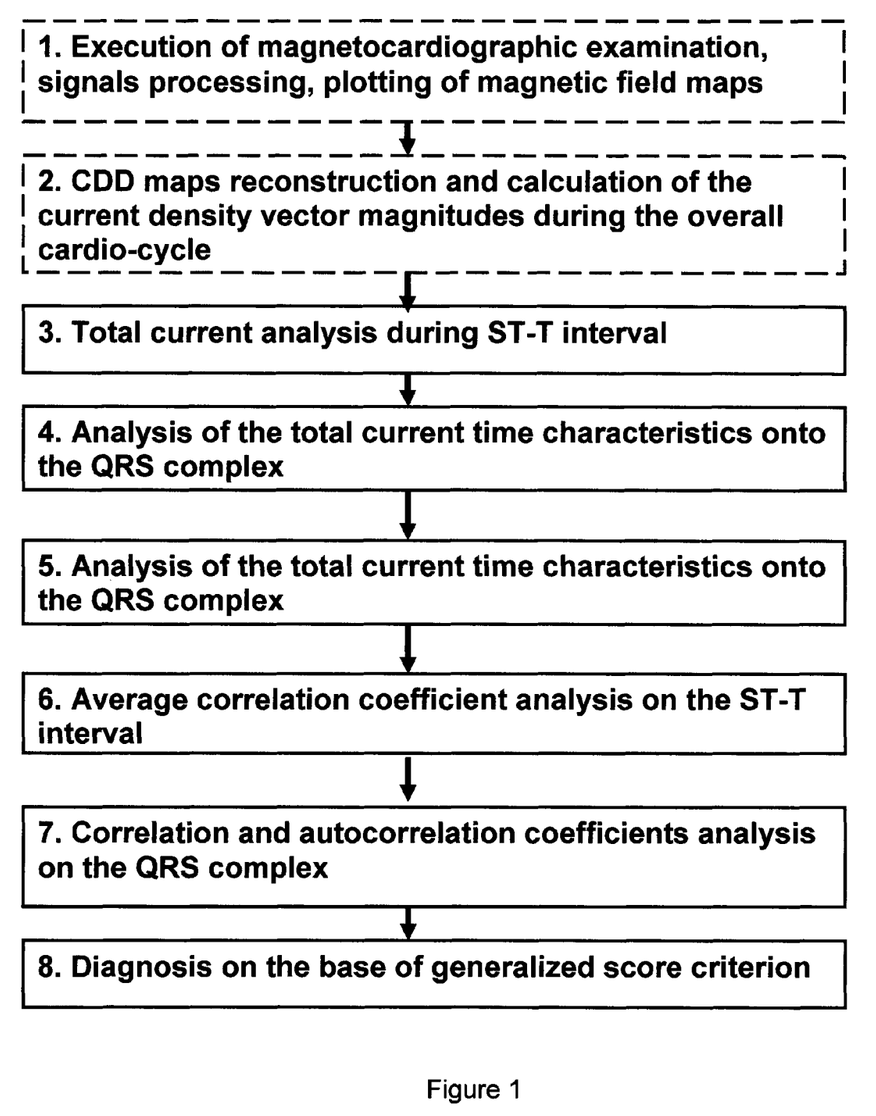
FIG. 1. Schematic diagram of method and device.

Step 1. Execution of MCG examination, preliminary signal processing and calculation of the magnetic field maps sets.

Particular implementation of proposed method covers preliminary carrying out of MCG examination with simultaneous ECG registration in 2-nd standard lead and processing of received data. Last one includes several actions: preliminary processing (filtering, rejection of complexes with pulse interferences, cardio-cycles selection of the same type and averaging), calculation of the MFM maps sets and reconstruction of CDD maps within the square area 20×20 cm. These actions are covered in patents UA 77722, UA 77723, UA 20101, UA 21299 and are not the subject matter of this invention.

Step 2. CDD maps reconstruction in the frontal plane and calculation of the current density vector magnitudes during the overall cardio-cycle.

CDD map—is a vector field, where vectors are placed onto the regular (usually square) grid. Each vector reflects the local values, i.e. current density in given point. Here inverse problem solution method is used according to WO/2002/00108 Computer-based method for automatically processing data, especially magnetocardiographic data, of biomagnetic fields. S. Romanovich, F. Steinberg, 20011 This approach was previously used in patents UA 83050, UA 83061, UA 90701 and prototype patent PCT/UA2011/000121 (UAa201107571). As a result one obtains CDD maps in the frontal plane, where vectors are placed onto the square grid 10×10 with 2 cm pitch.

Then magnitudes of the current density vectors are calculated. In the main implementation orthogonal projections of the vectors are calculated in 100 points of the map. Vector magnitudes are calculated using known formula for vector length expression by its projections. Calculations are performed sequentially for all CDD maps with time sampling rate 1 ms.

These actions are also similar to that in UA90701 and prototype PCT/UA2011/000121 (UAa201107571) and not the subject matter of this invention.

Figure 2:
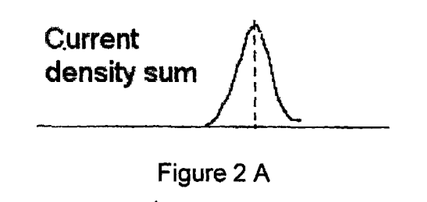

Step 3. Total current analysis during ST-T interval. This step includes execution of following actions:

3.1 Calculation of the total current for each map during the overall cardio-cycle;

3.2 Plotting the total current time variation curve during the ST-T interval. On FIG. 2. (a—injury is absent; b—significant injury) total current curve is represented onto ST-T interval (point J—beginning of the T wave). Vertical marker allocates the beginning point of T wave, which is determined as inflection point in the moment of rapid current intensity increase.

Figure 3:
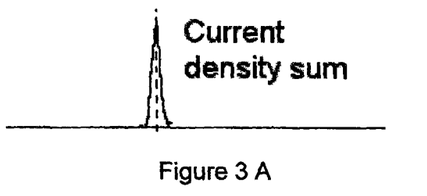
Figure 4:
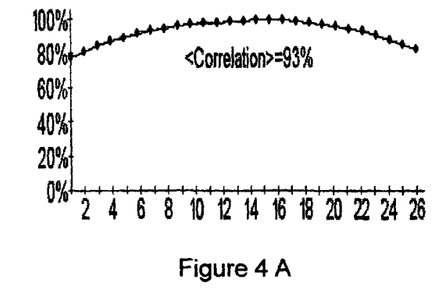
Figure 5:
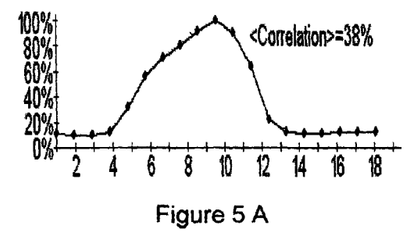
Figure 6:
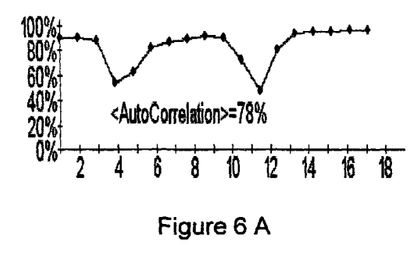

3.3 On the base of total current variation curve, according to item 3.1, calculation of the ST segment duration (point J-T wave beginning);

3.4 Calculation of the ratio of ST segment duration, according to item 3.2, to the overall ST-T interval duration;

3.5 Diagnosis of the ventricles injuries absence/presence according to the rule—injury is absent (minor, significant), if intervals ratio, according to item 3.4, is less than 25% (25-35%, more than 35%);

Step 4. Analysis of the total current time characteristics onto the QRS complex. This step includes execution of the following actions:

4.1. Calculation of the total current curve during QRS complex (point Q-point J) which describes complete ventricles depolarization, see FIG. 3, where vertical marker allocates point corresponding to the R wave peak (a—injury is absent; b—significant injury);

4.2. Diagnosis of the ventricles injuries absence/presence (minor, significant), if QRS complex duration is less than 0.11 s (0.11-0.14 s, more than 0.14 s);

4.3. Total current curves calculation for 4 time sub-intervals of the QRS complex, which represent depolarization of the interventricular septum (1), anterior wall and apex of the left ventricle LV (2), left ventricle side wall (3), basal myocardial regions (4);

4.4. Ratio calculation of 4 sub-intervals, according to item 4.3, to "appropriate" duration values, known from electrophysiology;

4.5. Diagnosis of absence/presence of (minor, significant) injury of myocardial regions (1)-(4) noted in item 4.3, if one of 4 sub-intervals ratio ranges from 0.8 to 1.2 (0.7-0.8 and 1.2-1.5, lower than 0.7 and higher than 1.5);

Step 5. Analysis of the total current-time characteristics onto the QRS complex. This step includes execution of the following actions:

5.1. Arithmetic mean value calculation of 4 sub-intervals ratios, calculated in item 4.4;

5.2. Diagnosis of the ventricles injuries absence/presence according to the rule—injury is absent (minor, significant), if arithmetic mean value, according to item 5.1, is ranged from 0.8 to 1.2 (0.7-0.8 and 1.2-1.5, lower than 0.7 and higher than 1.5);

5.3. In the case if during QRS complex there are negative waves occur, their quantity is counted;

5.4. Diagnosis of the ventricles injuries absence/presence according to the rule—injury is absent (minor, significant), if number of negative waves in QRS complex is less than 1 (is 2-3, more than 3);

Step 6. Correlation coefficient analysis during the ST-T interval. This step includes execution of following actions:

6.1. Time dependence calculation of the correlation coefficient for the instant map with map on the T wave peak during ST-T interval, see FIG. 4 (a—injury is absent; b—significant injury);

6.2. On the base of correlation curve, according to item 6.1, calculation of the ST segment duration (point J-T wave beginning);

6.3. Calculation of the ratio of ST segment duration, according to item 6.2, to the overall ST-T interval duration;

6.4. Diagnosis of the ventricles injuries absence/presence according to the rule—injury is absent (minor, significant), if intervals ratio, according to item 6.3, is less than 25% (25-35%, more than 35%);

6.5. Difference calculation between the maximum correlation coefficient on the T wave peak (which is equal to 1 by definition) and its value in the 4-th point of ST-T interval (40 ms after J point);

6.6. Diagnosis of the ventricles injuries absence/presence according to the rule—injury is absent (minor, significant), if said difference according to item 6.5, is less than 30% (30-50%, more than 50%);

6.7. Average correlation coefficient is calculated on the ST-T interval;

6.8. Diagnosis of the ventricles injuries absence/presence according to the rule—injury is absent (minor, significant), if average coefficient according to item 6.7, is more than 75% (60-75%, less than 60%);

Step 7. Correlation and autocorrelation coefficients analysis on the QRS complex. This step includes execution of the following actions:

7.1. Time dependence calculation of the correlation coefficient for the instant map with map on the R wave peak during QRS complex, see FIG. 5 (a—injury is absent; b—significant injury);

7.2. Diagnosis of the ventricles injuries absence/presence according to the rule—injury is absent (minor, significant), if correlation curve according to item 7.1 contains two (one, none) characteristic inflection points in the moments of rapid curve increase or decrease;

7.3. Diagnosis of the ventricles injuries absence/presence according to the rule—injury is absent (minor, significant), if said difference according to item 7.1, is less than 41% (41-60%, more than 60%);

7.4. Time dependence calculation of the autocorrelation coefficient for the instant map during QRS complex, see FIG. 6 (a—injury is absent; b—significant injury);

7.5. Diagnosis of the ventricles injuries absence/presence according to the rule—injury is absent (minor, significant), if autocorrelation curve according to item 7.4 contains two (one, none) expressed local minimums;

Step 8. Diagnosis on the base of generalized score criterion. This step includes execution of the following actions:

8.1. Assigning diagnosis "absence of injuries" 0 points, "presence of minor (significant) injury" 1(2) points;

8.2. Diagnosis of the ventricles injuries absence/presence according to the rule—injury is absent (minor, significant), if the sum of points according to item 8.1 for individual quantitative indicators according to items 3.5, 4.2, 4.5, 5.2, 5.4, 6.4, 6.6, 6.8, 7.2, 7.3, 7.5 is less than or equal to 7 (8-16, 17 and more);

In the main implementation all said actions, and calculations according to Steps 3-8 are implemented using device, including at least one electronic unit, controlled by embedded microprocessor. In other implementation at least one of said electronic modules is controlled using external computer.

Particular implementation of invented method is described in details just for the illustrative purposes. It's clear, that in practice, people experienced in MCG data analysis, and generally—in cardiology, could introduce some changes and modifications, for example, to split cardio-cycle intervals onto another number of sub-intervals, to use another merges for quantitative indicator intervals, to modify the score scale for different diagnoses by some parameters, to increase or decrease the number of its grades, to change averaging method for numerical indicators, or to introduce another interpretation of the absence, presence and severity degree of the myocardial injuries, etc. But we consider, that both said changes and modifications, and other ones, introduced without significant differences from the essence and claim of proposed invention, fall under this patent.

What is claimed is:

1. Method for evaluation of myocardial damage based on evaluating and scoring current density variations derived from magnetocardiographic data, wherein indication of ventricular damage is determined based evaluating and scoring of eleven quantitative indicators, comprising:

reconstructing current density distribution maps in the frontal plane and calculating current density vector lengths for each map during the cardio-cycle, and wherein the QRS complex of the cardio-cycle is divided into four sub-intervals (1)-(4), which represent the (1) depolarization of the interventricular septum, (2) anterior wall and apex of the left ventricle LV, (3) left ventricle side wall, and (4) basal myocardial regions; and generating a score for each of eleven following indicators:

(1) wherein the total current for each density distribution map is calculated during the cardio-cycle, and the total current curve is plotted onto the ST-T interval, and the ST segment duration is calculated as point J to T wave beginning, and the ratio of the ST segment duration to the ST-T interval duration is obtained, and, wherein diagnosis is made concerning absence of, presence of minor, or presence of significant ventricular damage, if said ratio is less than 25%, 25% to 35%, or more than 35%, respectively;

(2) wherein, a curve of total current is calculated during the QRS complex as Q point to J point, and diagnosis is made concerning absence of, presence of minor, or presence of significant, ventricular damage, if the QRS complex duration is less than 0.11 s, 0.11 s to 0.14 s, or more than 0.14 s, respectively;

(3) wherein curves of total current are calculated for the four-sub-intervals (1)-(4) of the QRS complex and the ratios of the curves of total current to the corresponding expected values known from electrophysiology are derived, and diagnosis is made concerning absence of, presence of minor, or presence of significant ventricular damage, according to whether one of the four ratios, is ranged from 0.8 to 1.2, from 0.7 to 0.8 or 1.2 to 1.5, or lower than 0.7 or higher than 1.5, respectively:

(4) wherein an arithmetic mean is calculated of the four ratios and diagnosis is made concerning absence of, presence of minor, or presence of significant ventricular damage, if the calculated arithmetic mean is ranged from 0.8 to 1.2, from 0.7 to 0.8 or 1.2 to 1.5, or lower than 0.7 or higher than 1.5, respectively;

(5) wherein the QRS complex contains negative waves, the negative waves are counted and diagnosis made concerning absence of, presence of minor, or presence of significant ventricular damage, if the number of negative waves is less than 1, from 2 to 3, or more than 3, respectively;

(6) wherein a time dependence is calculated of the correlation coefficient for an instant map with a map taken on the T wave peak during the ST-T interval, from which a ratio of ST segment duration to ST-T interval duration is calculated, and diagnosis is made concerning absence of, presence of minor, or presence of significant ventricular damage, if said ratio is less than 25%, 25% to 35%, or more than 35%, respectively;

(7) wherein a difference is calculated between the maximum correlation coefficient on the T wave peak and its value in the fourth point of ST-T interval, which is 40 ms after J point, and diagnosis is made concerning absence of, presence of minor, or presence of significant ventricular damage, if said difference is less than 30%, from 30% to 50%, or more than 50%, respectively;

(8) wherein a time dependence is calculated of the correlation coefficients for an instant map with a map taken on the R-wave peak during the QRS complex, and diagnosis is made concerning absence of, presence of minor, or presence of significant ventricular damage, if a curve of the time dependence at moments of rapid curve increase/decrease contains respectively, 2, 1, or 0 characteristic inflection points;

(9) wherein a time dependence is calculated of the autocorrelation coefficient for an instant map during the QRS complex, and diagnosis is made concerning absence of, presence of minor, or presence of significant ventricular damage, if a curve of the time dependence contains respectively, 2, 1, or 0;

(10) wherein average correlation coefficients are calculated on the ST-T interval and QRS complex and diagnosis is made concerning absence of, presence of minor, or presence of significant ventricular damage, if the average correlation coefficient on the ST-T interval is higher than 75%, 60% to 75%, or lower than 60%, respectively, and;
(11) a diagnosis is make concerning absence of, presence of minor, or presence of significant ventricular injury, wherein, if the average correlation coefficient on the QRS complex is lower than 41%, 41% to 60%, or more than 60%, respectively;

wherein each quantitative indicator is scored with 0 points if a diagnosis of absence of ventricular damage is made for that quantitative indicator, with 1 point if a diagnosis of presence of minor ventricular damage is made for that quantitative indicator, and with 2 points if a diagnosis of presence of significant damage is made for that quantitative indicator; and wherein, an overall diagnosis is provided concerning absence of, presence of minor, or presence of significant ventricular damage, if the sum of points for all said quantitative indicators is less than or equal to 7, from 8 to 16, or 17 or more, respectively.

2. Device for evaluation of myocardial damages based on-magnetocardiographic data representing current density variations, implemented with at least one electronic unit, wherein said electronic unit is configured to receive the magnetocardiographic data and based on these data perform the following steps:

current density distribution maps are reconstructed in the frontal plane and current density vectors lengths are calculated for each map during the cardio-cycle;

the QRS complex is divided into four sub-intervals (1)-(4), which represent respectively depolarization of the interventricular septum (1), anterior wall and apex of the left ventricle LV (2), left ventricle side wall (3), and basal myocardial regions (4);

the total current for each map is calculated during the cardio-cycle, total current curve is plotted onto the ST-T interval, ST segment duration is calculated as point J to T wave beginning, the ratio of the ST segment duration to the ST-T interval duration is obtained, and diagnosis is made concerning absence of, presence of minor, or presence of significant ventricular damage, if said ratio is less than 25%, 25% to 35%, or more than 35%, respectively, to obtain thereby a first quantitative indicator;

a curve of total current is calculated during the QRS complex as Q point to J point, and diagnosis is made concerning absence of, presence of minor, or presence of significant ventricular damage, if the QRS complex duration is less than 0.11 s, 0.11 s to 0.14 s, or more than 0.14 s, respectively, to obtain thereby a second quantitative indicator;

curves of total current are calculated for the four sub-intervals (1)-(4) of the QRS complex and the ratios of the curves of total current to the corresponding expected values known from electrophysiology are derived, and diagnosis is made concerning absence of, presence of minor, or presence of significant ventricular damage, according to whether one of the four ratios is ranged from 0.8 to 1.2, from 0.7 to 0.8 or 1.2 to 1.5, or lower than 0.7 or higher than 1.5, respectively, to obtain thereby a third quantitative indicator:

an arithmetic mean is calculated of the four ratios and diagnosis is made concerning absence of, presence of minor, or presence of significant ventricular damage, if the calculated arithmetic mean is ranged from 0.8 to 1.2, from 0.7 to 0.8 or 1.2 to 1.5, or lower than 0.7 or higher than 1.5, respectively, to obtain thereby a fourth quantitative indicator;

if the QRS complex contains negative waves, the negative waves are counted and diagnosis made concerning absence of, presence of minor, or presence of significant ventricular damage, if the number of negative waves is less than 1, from 2 to 3, or more than 3, respectively, to obtain thereby a fifth quantitative indicator;

a time dependence is calculated of the correlation coefficient for an instant map with a map taken on the T wave peak during the ST-T interval, from which a ratio of ST segment duration to ST-T interval duration is calculated, and diagnosis is made concerning absence of, presence of minor, or presence of significant ventricular damage, if said ratio is less than 25%, 25 to 35%, or more than 35%, respectively, to obtain thereby a sixth quantitative indicator;

a difference is calculated between the maximum correlation coefficient on the T wave peak and its value in the 4th point of ST-T interval, which is 40 ms after J point, and diagnosis is made concerning absence of, presence of minor, or presence of significant ventricular damage, if said difference is less than 30%, from 30% to 50%, or more than 50%, respectively, to obtain thereby a seventh quantitative indicator;

a time dependence is calculated of the correlation coefficient for an instant map with a map taken on the R-wave peak during the QRS complex, and diagnosis is made concerning absence of, presence of minor, or presence of significant ventricular damage, if a curve of the time dependence at moments of rapid curve increase/decrease contains respectively, 2, 1, or 0 characteristic inflection points, to obtain thereby an eighth quantitative indicator;

a time dependence is calculated of the autocorrelation coefficient for an instant map during the QRS complex, and diagnosis is made concerning absence of, presence of minor, or presence of significant ventricular damage, if a curve of the time dependence contains respectively, 2, 1, or 0 local minima, to obtain thereby a ninth quantitative indicator;

average correlation coefficients are calculated on the ST-T interval and QRS complex and diagnosis is made concerning absence of, presence of minor, or presence of significant ventricular injury, if the average correlation coefficient on the ST-T interval is higher than 75%, 60% to 75%, or lower than 60%, respectively, to obtain a tenth quantitative indicator, and a diagnosis is make concerning absence of, presence of minor, or presence of significant ventricular injury, if the average correlation coefficient on the QRS complex is lower than 41%, 41% to 60%, or more than 60%, respectively, to obtain an eleventh quantitative indicator;

each quantitative indicator is scored with 0 points if a diagnosis of absence of ventricular damage is made for that quantitative indicator, with 1 point if a diagnosis of presence of minor ventricular damage is made for that quantitative indicator, and with 2 points if a diagnosis of presence of significant damage is made for that quantitative indicator; and an overall diagnosis is provided concerning absence of, presence of minor, or presence of significant, ventricular damage, if the sum of points for all said quantitative indicators is less than or equal to 7, from 8 to 16, or 17 or more, respectively.

3. A method for evaluation of myocardial damages comprising:

reconstructing current density distribution maps from magnetocardiographic data in the frontal plane and calculating current density vectors lengths for each map during the QRS complex cardio-cycle, wherein the QRS complex is divided into four sub-intervals (1)-(4), which represent the (1) depolarization of the interventricular septum, (2) anterior wall and apex of the left ventricle LV, (3) left ventricle side wall, and (4) basal myocardial regions; and generating a score for each of eleven indicators, provided that each quantitative indicator is scored with 0 points if a diagnosis of absence of ventricular damage is made for that quantitative indicator, with 1 point if a diagnosis of presence of minor ventricular damage is made for that quantitative indicator, and with 2 points if a diagnosis of presence of significant damage is made for that quantitative indicator; wherein the eleven quantitative indicators consist of the following indicators:

(1) wherein the total current for each map is calculated during the cardio-cycle, and the total current curve is plotted onto the ST-T interval, and the ST segment duration is calculated as point J to T wave beginning, and the ratio of the ST segment duration to the ST-T interval duration is obtained, and, wherein diagnosis is made concerning absence of, presence of minor, or presence of significant ventricular damage, if said ratio is less than 25%, 25% to 35%, or more than 35%, respectively;

(2) a curve of total current is calculated during the QRS complex as Q point to J point, and diagnosis is made concerning absence of, presence of minor, or presence of significant ventricular damage, if the QRS complex duration is less than 0.11 s, 0.11 to 0.14 s, or more than 0.14 s, respectively;

(3) curves of total current are calculated for the four sub-intervals (1)-(4) of the QRS complex and the ratios of the curves of total current to the corresponding expected values known from electrophysiology are derived, and diagnosis is made concerning absence of, presence of minor, or presence of significant ventricular damage according to whether one of the four ratios, is ranged from 0.8 to 1.2, from 0.7 to 0.8 or 1.2 to 1.5, or lower than 0.7 or higher than 1.5, respectively;

(4) an arithmetic mean is calculated of the four ratios and diagnosis is made concerning absence of, presence of minor, or presence of significant ventricular damage, if the calculated arithmetic mean is ranged from 0.8 to 1.2, from 0.7 to 0.8 or 1.2 to 1.5, or lower than 0.7 or higher than 1.5, respectively;

(5) the QRS complex contains negative waves, the negative waves are counted and diagnosis made concerning absence of, presence of minor, or presence of significant ventricular damages, if the number of negative waves is less than 1, from 2 to 3, or more than, respectively;

(6) a time dependence is calculated of the correlation coefficient for an instant map with a map taken on the T wave peak during the ST-T interval, from which a ratio of ST segment duration to ST-T interval duration is calculated, and diagnosis is made concerning absence of, presence of minor, or presence of significant ventricular damage, if said ratio is less than 25%, 25% to 35%, or more than 35%, respectively;

(7) a difference is calculated between the maximum correlation coefficient on the T wave peak and its value in the fourth point of ST-T interval, which is 40 ms after J point, and diagnosis is made concerning absence of, presence of minor, or presence of significant ventricular damage, if said difference is less than 30%, from 30% to 50%, or more than 50%, respectively;

(8) a time dependence is calculated of the correlation coefficients for an instant map with a map taken on the R-wave peak during the QRS complex, and diagnosis is made concerning absence of, presence of minor, or presence of significant ventricular damage, if a curve of the time dependence at moments of rapid curve increase/decrease contains respectively 2, 1, or 0 characteristic inflection points;

(9) a time dependence is calculated of the autocorrelation coefficient for an instant map during the QRS complex, and diagnosis is made concerning absence of, presence of minor, or presence of significant ventricular damage, if a curve of the time dependence contains respectively, 2, 1, or 0 local minimum;

(10) average correlation coefficients are calculated on the ST-T interval and QRS complex and diagnosis is made concerning absence of, presence of minor, or presence of significant ventricular injury, if the average correlation coefficient on the ST-T interval is higher than 75%, 60% to 75%, or lower than 60%, respectively, to obtain a tenth quantitative indicator; and (11) a diagnosis is make concerning absence of, presence of minor, or presence of significant ventricular injury, if the average correlation coefficient on the QRS complex is lower than 41%, 41% to 60%, or more than 60%, respectively; and wherein, an overall diagnosis is provided concerning absence of, presence of minor, or presence of significant ventricular damage, if the sum of points for all said quantitative indicators is less than or equal to 7, from 8 to 16, or 17 or more, respectively.

* * * * *

UNITED STATES PATENT AND TRADEMARK OFFICE
CERTIFICATE OF CORRECTION

PATENT NO. : 9,451,901 B2  
APPLICATION NO. : 14/376928  
DATED : September 27, 2016  
INVENTOR(S) : Illya Anatoliiovych Chaykovskyy Page 1 of 1

It is certified that error appears in the above-identified patent and that said Letters Patent is hereby corrected as shown below:

Claims

Column 11, line 3, Claim 1, the word "make" should read --made--.

Column 12, line 48, Claim 2, the word "make" should read --made--.

Column 14, line 43, Claim 3, the word "make" should read --made--.

Signed and Sealed this  
Fifteenth Day of November, 2016

Michelle K. Lee  
*Director of the United States Patent and Trademark Office*